United States Patent [19]

Matsumoto et al.

[11] 4,384,041

[45] May 17, 1983

[54] ASSAY METHOD OF ENZYME ACTIVITY

[75] Inventors: Kunio Matsumoto, Mishima; Toshiharu Noda, Shizuoka; Tadashiro Fujii, Mishima; Susumu Watanabe, Shizuoka; Kazuhiko Matsumoto, Mishima; Shigeo Katsuragi, Shizuoka, all of Japan

[73] Assignee: Toyo Jozo Kabushiki Kaisha, Shizuoka, Japan

[21] Appl. No.: 251,784

[22] Filed: Apr. 7, 1981

[30] Foreign Application Priority Data

Apr. 7, 1980 [JP] Japan .................................. 55-46085
Dec. 4, 1980 [JP] Japan .............................. 55-171263

[51] Int. Cl.³ .................. C12N 11/00; C12Q 1/26; C12Q 1/28; C12Q 1/36
[52] U.S. Cl. ........................................ 435/24; 435/25; 435/28; 435/174; 435/817
[58] Field of Search ................... 435/24, 25, 28, 174, 435/817

[56] References Cited

FOREIGN PATENT DOCUMENTS 53-65787  6/1978  Japan ..................................... 435/24
1199565  7/1970  United Kingdom ................... 435/25

OTHER PUBLICATIONS

Whitaker, *Principles of Enzymology for the Food Sciences*, Marcel Dekker, Inc., New York, 352-353, (1972).

*Primary Examiner*—Esther M. Kepplinger
*Attorney, Agent, or Firm*—Young & Thompson

[57] ABSTRACT

Novel amine compounds of the formula

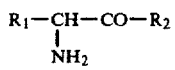

wherein $R_1$ is lower alkyl and $R_2$ is substituted methyl amino or D-amino acid residue, or a salt thereof. $R_1$ can typically be isobutyl or methyl; and $R_2$ can be methylamino of the formula

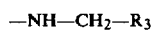

in which $R_3$ is organic, more particularly methyl, ethyl, n-propyl, isopropyl, n-butyl, amyl, p-hydroxybenzyl, 3,4-di-hydroxybenzyl, 5-imidazolemethyl, 3-imidazolemethyl or phenyl. $R_2$ can also be D-amino acid residue of the formula

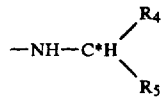

in which one of $R_4$ and $R_5$ is carboxyl and the other is organic, more particularly methylthioethyl, isobutyl, methyl or phenyl, and C* is a D-asymmetric carbon atom. The compounds are useful in an assay method for leucine and aminopeptidase which comprises reacting a substrate amide as above, or a salt thereof, with a sample for leucine aminopeptidase assay, incubating the reaction product produced thereby, and measuring the thus-consumed oxygen or liberated hydrogen peroxide.

10 Claims, 11 Drawing Figures

ASSAY METHOD OF ENZYME ACTIVITY

This invention relates to assay methods of enzyme activity, using as a substrate a compound of the formula $$R_1-CH-CO-R_2 \atop NH_2 \qquad \text{[I]}$$

wherein $R_1$ is lower alkyl and $R_2$ is substituted methylamino or D-amino acid residue, or a salt thereof.

Leucine aminopeptidase [α-aminoacyl-peptide hydrolase (cytosol), EC 3. 4. 11. 1., hereinafter designated LAP; formerly L-leucylpeptide hydrolase, EC 3. 4. 1.1] is distributed in tissues and serum, and is known to increase under disease conditions. LAP assay is used for the clinical diagnosis of various disease and the observation of prognosis.

The analytical unit of LAP is defined as a G-R unit (Goldbarg Rutenburg). The G-R unit = 2.72 × LAP international unit (mU/ml). [Cancer. 11, 283 (1958)].

A number of assay methods for LAP are known. However, each known method has disadvantages. Conventional assay methods are the colorimetry of amine compounds produced by enzymatic action on a synthetic substrate consisting of L-leucine and an amine compound. When a synthetic substrate such as L-leucine-p-nitroanilide is incubated with LAP, a wave length of the yellow color of p-nitroaniline formed by the enzymatic action is overlapped upon colorimetric assay, and moreover the serum composition, especially bilirubin pigment, affects the colorimetry. Furthermore, when L-leucine-β-naphthyl-amide is used as substrate, the color formed is colorimetrically measured, for example, by coupling the formed β-naphthylamine with 5-nitro-2-amino-methoxybenzene diazotate; coupling the diazotated β-naphthylamine by sodium nitrate with N-(1-naphthyl)-ethylenediamine; or condensating the β-naphthylamine with p-dimethylaminobenzaldehyde or p-dimethylamino cinnamaldehyde. These colorimetric assay methods have a number of disadvantages such as complex reaction process and the requirement of strict observance of the operating procedures. Moreover the formed β-naphthylamine is high in toxicity and is carcinogenic for the bladder.

Another enzymatic assay method for LAP activity is that in which L-leucineamide is used as substrate for LAP and the formed ammonia is incubated with α-ketoglutarate, glutamate dehydrogenase and NADH$_2$ to transform glutamic acid, then the oxidized NADH$_2$ is spectrophotometrically measured. When the substrate L-leucyl-L-alanine is used, L-alanine liberated by LAP is incubated with α-ketoglutarate and glutamic-pyruvic transaminase to form pyruvic acid which is converted to lactic acid by lactate dehydrogenase, wherein consumed NADH$_2$ is subjected to spectrophotometric assay.

A further assay method using L-leucine dehydrogenase is known. L-leucine liberated from L-leucyl-glycine by LAP is incubated with L-leucine dehydrogenase, then NADH$_2$ is spectrophotometrically measured. (Japanese Patent Open No. 54-119290). Furthermore, L-leucinamide is used as substrate and the formed L-leucine is incubated with L-amino acid oxidase to liberate hydrogen peroxide which is subjected to colorimetric assay. [Pharmacia, 14, 872 (1978)].

These prior known enzymatic assay methods have a number of disadvantages. For example, the enzymatic reaction system is complicated, and bilirubin pigment or emulsified serum affects the colorimetric assay. In the assay method using L-amino acid oxidase, L-amino acid in the blood inhibits the assay of L-leucine liberated by LAP; moreover, the amount of L-amino acid in the blood is not constant, which causes difficulties during assay.

We have found that LAP hydrolyzes the substrates synthesized from substituted methylamine, which does not exist in the blood, such as benzylamine, tyramine or butylamine, or D-amino acid such as D-methionine or D-leucine, and L-leucine or L-alanine to liberate with good yield a substituted methylamine such as tyramine or D-amino acid. The liberated substituted methylamine or D-amino acid is oxidized by the corresponding oxidase and the amount of consumed oxygen or liberated hydrogen peroxide is measured, thereby assaying the activity of the LAP. Further, we have found a novel useful synthetic substrate amide compound of the formula [I]

$$R_1-CH-CO-R_2 \atop NH_2 \qquad \text{[I]}$$

wherein $R_1$ and $R_2$ have the same meanings as hereinbefore.

Embodiments of this synthetic substrate are amide compounds of the formula [I] which are synthesized from L-leucine or L-alanine and substituted methylamine or D-amino acid, wherein $R_1$ is lower alkyl such as isobutyl or methyl, and $R_2$ is substituted methylamino of the formula [II]

$$-NH-CH_2-R_3 \qquad \text{[II]}$$

wherein $R_3$ is an organic group, or $R_2$ is a D-amino acid residue of the formula [III]

$$-NH-C^*H{\overset{\displaystyle R_4}{\underset{\displaystyle R_5}{\diagdown}}} \qquad \text{[III]}$$

wherein one of $R_4$ and $R_5$ is carboxyl, the other is an organic residue, and C* is D-asymmetric carbon. Examples of the organic group $R_3$ are methyl, ethyl, n-propyl, isopropyl, n-butyl, amyl, p-hydroxybenzyl, 3,4-dihydroxybenzyl, 5-imidazolmethyl, 3-indolmethyl and phenyl. Examples of the groups $R_4$ and $R_5$ are that one of $R_4$ and $R_5$ is carboxyl and the other is methylthioethyl, isobutyl, methyl or phenyl. Examples of substituted methylamine or D-amino acid are, for example, ethylamine, n-propylamine, n-butylamine, iso-butylamine, n-amylamine, n-hexylamine, tyramine, 3,4-dihydroxyphenylethylamine, histamine, tryptamine, benzylamine, D-methionine, D-leucine, D-alanine and D-phenylglycine.

Embodiments of the said substituted amines are compounds consisting of L-leucine and substituted methylamine such as L-leucine-benzylamide, L-leucine-p-hydroxyphenylethylamide and L-leucine-n-butylamide, a compound consisting of L-leucine and D-amino acid such as L-leucyl-D-methionine and L-Leucyl-D-leucine, or a compound consisting of L-alanine and substituted methylamine such as L-alanine-p-hydroxyphenylethylamide. These substituted amines can be used as soluble salts such as hydrochloride, hydrobromide, phosphate, formate, acetate, propionate or oxalate.

An amide compound of the present invention can be produced by a conventional peptide synthesis such as protection and removal of the protective group and a condensation reaction.

Examples of the protective group for α-amino group in L-amino acid, such as L-alanine and L-leucine, of the formula [IV]

[IV]

wherein $R_1$ has the same meanings as hereinbefore, are conventional protective groups such as t-butoxycarbonyl, t-amyloxycarbonyl, adamantyloxycarbonyl, benzyloxycarbonyl, o-nitrophenylthio or nitro-substituted benzyloxycarbonyl. The carboxyl group can be transformed to an activated form such as acid azide, mixed anhydride, acid imidazolide or activated ester, for example cyanomethyl ester, p-nitrophenyl ester, 2,4-dinitrophenyl ester, N-hydroxysuccinimide ester or N-hydroxyphthalimide ester, or activated by using carbodiimide, N,N'-carbonyldiimidazole or an isoxazolium salt such as Woodward reagent. These activated forms of the L-amino acid are reacted with a substituted methylamine compound or D-amino acid by a condensation reaction such as the carbodiimide method, activated ester method or acid anhydride method. The reaction is carried out in an inert solvent such as dimethylformamide, dimethylacetamide, dimethylsulfoxide or tetrahydrofurane, with an equi-molar ratio of the compound, at $-30°$ C. to ambient temperature with stirring. The reaction can be terminated after 5 to 50 hours. Thereafter, the protective group can be removed. The t-butoxycarbonyl group can be removed by trifluoroacetic acid, and the benzyloxycarbonyl group is removed by catalytic reduction with palladium-carbon. The product can be purified by extraction, washing, chromatography or crystallization. The thus-obtained product is transformed to its salt, for example an inorganic salt such as hydrochloride, hydrobromide or phosphate, or an organic acid salt such as formate, acetate, propionate or oxalate.

Oxidase corresponding to the substitute methylamine and D-amino acid liberated by the action of LAP on the above synthetic substrate of the present invention is at least an enzyme which hydrolyzes these substituted methylamines or D-amino acids as substrate to consume oxygen and liberate hydrogen peroxide in an enzymatic reaction. Examples of the enzyme for substituted methylamine are an amine oxidase such as monoamine oxidase, diamine oxidase or polyamine oxidase; and the enzyme for D-amino acid is D-amino acid oxidase. Monoamine oxidase is an enzyme obtained from porcine or bovine serum and *Aspergillus niger;* tyramine oxidase is an enzyme of *Sarcina lutea* IAM 1099 [Biochem. Biophys. Res. Commn., 27, 350 (1967), Methods in Enzymology, 17, 722 (1971)]; and D-amino acid oxidase is an enzyme from animal tissues or *Trigonopsis variavillis.*

These oxidases may be used in an immobilized form. The immobilized enzyme can be assembled in an automatic analyzer, and is used in combination with an oxygen electrode or a hydrogen peroxide electrode. The immobilized form has advantages for reducing the amount of valuable and expensive enzymes. The sensor comprising the combination of the immobilized enzyme of enzyme electrode and the above electrodes can be used for rapid and multiple measuring without various reagents. The sensor can also be advantageously used in colored samples for assaying LAP activity.

The immobilized enzyme can be prepared by known immobilization techniques, for example entrapping with acrylamide, cross-linking with proteins by mixing with albumin, entrapping with collagen and fibroin or covalently bonding therewith, adsorption or covalent bonding with a porous organic polymer or entrapping with photoresist. These immobilized enzymes are processed for membrane, fibrous forms, pellets or tubes suitable for enzyme electrodes.

An embodiment of the LAP activity assay is as follows:

An aliquot portion of synthetic substrate solution is incubated with a LAP assay sample such as serum in a buffer. Incubation is carried out at 37° C. Incubation time need not be limited but is preferably the time necessary for liberating substituted amine or D-amino acid from the synthetic substrate by LAP. The thus-liberated substituted methylamine or D-amino acid is oxidized by the corresponding oxidase to consume oxygen or to liberate hydrogen peroxide. The reaction is effected by adding the corresponding oxidase solution or contacting the reaction mixture with immobilized oxidase at 37° C. The thus-consumed oxygen or liberated hydrogen peroxide is preferably measured by an oxygen electrode or a hydrogen peroxide electrode. This assay is advantageously performed with the enzyme electrode comprising the combination of the immobilized enzyme and the electrode. The output is recorded or displayed as electric consumption to convert LAP activity. The amount of hydrogen peroxide is conventionally measured by a coloration reagent consisting of 4-aminoantipyrine, phenol and peroxidase, or a luminescent reagent such as luminol.

An embodiment of an LAP activity assay method is a reaction-detection method comprising injecting LAP-activity-measuring reagent, substrate solution and buffer into an LAP reactor vessel in which the substituted methylamine or D-amino acid is liberated from the synthetic substrate, oxidizing the thus-formed substituted methylamine or D-amino acid by the corresponding oxidase, and detecting the amount of oxygen consumed or hydrogen peroxide liberated.

In the reaction-detector system, the immobilized enzyme column part of oxidase and the detection electrode part may preferably be separated, or unitarily constructed as an enzyme electrode wherein the immobilized enzyme is attached to the detector of the electrode. The assay system can be a multiple reactor-detector system in which, for example, sampling is taken from multiple LAP reactors to inject the reaction-detector vessel, followed by detections and washings.

In the examples, an assay system using an oxygen electrode is given, by way of example. However, in this invention, a hydrogen peroxide electrode can also be advantageously used.

The LAP assay method of the present invention is quite simple, rapid and reproducible, and is quite useful for clinical diagnosis.

The abbreviations in the following description have the following meansings:

Boc: t-butoxycarbonyl
HOSu: N-hydroxysuccinimide
OSu: N-hydroxysuccinimide ester
DCC: N,N'-dicyclohexylcarbodiimide
THF: tetrahydrofuran
DCU: N,N'-dicyclohexylurea
DMF: dimethylformamide
NMM: N-methylmorpholine
TFA: trifluoroacetic acid
Z: benzyloxycarbonyl The following examples illustrate the present invention but are not to be construed as limiting:

EXAMPLE 1

L-Leu-NH-CH$_2$-C$_6$H$_5$ (L-leucine-benzylamide)

Boc-Leu-OSu (3.28 g, 10 mM) and benzylamine (1.07 g, 10 mM) dissolved in DMF (30 ml) was adjusted to pH 7 by adding NMM, and the mixture was stirred overnight at room temperature. DMF was distilled off and the residue was dissolved in ethyl acetate. The solution was washed three times with 5% w/w sodium bicarbonate solution, twice with 1 N-HCl and twice with water, dehydrated with sodium sulfate, then ethyl acetate was distilled off. The residue was charged on a column of silica gel (100 g) and eluted with benzene-ethyl acetate (1:1) to obtain Boc-Leu-NH-CH$_2$-C$_6$H$_5$ (1.3 g).

This compound (1.2 g) dissolved in TFA (3 ml) was stirred for 30 minutes. After TFA was distilled off, the residue was dissolved in 0.1 N acetic acid. The solution was charged on a column of Sephadex LH-20 (97.0×3.0 cm) and fractionated into fractions of 6.3 ml each. Fractions Nos. 28-36 were collected and lyophilized to obtain L-leucine-benzylamide acetate (900 mg).

Yield: 32.1% (acetate)

Molecular formula: C$_{13}$H$_{20}$N$_2$O.CH$_3$COOH

Elementary analysis:

|  | C % | H % | N % |
|---|---|---|---|
| Calculated: | 64.26 | 8.63 | 9.99 |
| Found: | 64.22 | 8.68 | 10.01 |

Rf value: silica gel plate (n-butanol:acetic acid:water=3:1:1), Rf=0.80

IR (Nujol): 1690, 1620 cm$^{-1}$ (—CO—NH—)

EXAMPLE 2

L-Leu-D-Met-OH (L-leucyl-D-methionine)

D-Met-OH (1.4 g, 10 mM) and sodium bicarbonate (1.68 g, 20 mM) were added to a mixture of water (15 ml) and DMF (5 ml). Boc-Leu-OSu (3.28 g, 10 mM) in DMF (30 ml) was added thereto and the mixture was stirred overnight at room temperature. After cooling to 0° C., the pH was adjusted to pH 6.5 with 1 N-HCl and the solution was concentrated in vacuo. The residue was dissolved in ethyl acetate-1 N-HCl (50 ml-50 ml). The ethyl acetate layer was washed with water, dried by adding sodium sulfate and ethyl acetate was distilled off. The residue was charged on a column of silica gel (100 g) and eluted with benzene-ethyl acetate (1:1) to obtain Boc-Leu-D-Met-OH (1.6 g).

This product (1.5 g) was dissolved in TFA (4 ml) and stirred at room temperature for 30 minutes. After TFA was distilled off, the residue was dissolved in 0.1 N acetic acid and charged on a column of Sephadex LH-20 (97.0×3.0 cm) to produce fractions of 6.3 ml each. Fractions Nos. 28-36 were collected and lyophilized to yield L-leucyl-D-methionine acetate (1.3 g).

Yield: 40.4%

Molecular formula: C$_{11}$H$_{22}$N$_2$SO$_3$.CH$_3$COOH

Elementary analysis:

|  | C % | H % | N % | S % |
|---|---|---|---|---|
| Calculated: | 48.43 | 8.13 | 8.69 | 9.94 |
| Found: | 48.40 | 8.15 | 8.65 | 9.95 |

Rf value: silica gel plate (n-butanol:acetic acid:water=3:1:1), Rf=0.50

IR (Nujol): 1687, 1620 cm$^{-1}$ (—CO—NH—)

EXAMPLE 3

L-Leuc-NH-CH$_2$-CH$_2$-C$_6$H$_5$-OH (L-leucine-p-hydroxyphenylethylamide)

Boc-Leu-OSu (3.28 g, 10 mM) and tyramine (1.37 g, 10 mM) dissolved in DMF (30 ml) were adjusted to pH 7 with NMM at 0° C. and the mixture was stirred overnight at room temperature. After DMF was distilled off, the residue was dissolved in ethyl acetate (50 ml), washed three times with 5% w/w sodium bicarbonate solution, twice with 1 N-HCl and twice with water, and then dried by adding sodium sulfate. After the ethyl acetate was distilled off, the residue was charged on a column of silica-gel (100 g), and eluted with benzene-ethyl acetate (1:1) to obtain Boc-Leu-NH-CH$_2$-CH$_2$-C$_6$H$_4$-OH (1.58 g).

This compound (1.4 g) was dissolved in TFA (5 ml), stirred for 30 minutes at room temperature and TFA was distilled off. The residue dissolved in 0.1 N acetic acid was charged on a column of Sephadex LH-20 (97.0×3.0 cm) to produce fractions of 6.3 ml each. Fractions Nos. 30-38 were collected and lyophilized to yield L-leucine-p-hydroxyphenylethylamide acetate (1.25 g).

Yield: 40.3% (acetate)
Molecular formula: $C_{14}H_{22}N_2O_2 \cdot CH_3COOH$
Elementary analysis:

|  | C % | H % | N % |
|---|---|---|---|
| Calculated: | 61.92 | 8.44 | 9.03 |
| Found: | 61.90 | 8.45 | 9.02 |

Rf value: silica gel plate (n-butanol:acetic acid:-water=3:1:1), Rf=0.75
IR (Nujol): 1685, 1615 cm$^{-1}$ (—CO—NH—)

EXAMPLE 4

L-Leu-NH-(CH$_2$)$_3$-CH$_3$ (L-leucine-n-butylamide):

Boc-Leu-OH (2.5 g, 10 mM), n-butylamine (1 ml, 1 mM) and 1-hydroxybenztriazole (2.7 g) were dissolved in THF (25 ml) and cooled in an ice bath. Water-soluble carbodiimide (1.83 ml, 1 mM) was added thereto and the mixture was stirred overnight. After THF was distilled off, residue was dissolved in ethyl acetate (50 ml), which was washed three times with 5% w/w sodium bicarbonate solution, twice with 1 N-HCl and twice with water, then dried with sodium sulfate and ethyl acetate was distilled off. The residue was charged on a column of silica gel (100 g) and eluted with benzene-ethyl acetate (1:1) to obtain Boc-Leu-NH-(CH$_2$)$_3$ (1.4 g).

This compound (1.2 g) was dissolved in TFA (3 ml), stirred for 30 minutes at room temperature then TFA was distilled off. The residue dissolved in 0.1 N acetic acid was charged on a column of Sephadex LH-20 (97.0×3.0 cm) and fractionated to produce fractions of 6.3 ml each. Fractions Nos. 30-35 were collected and lyophilized to obtain L-leucine-n-butylamide acetate (800 mg).

Yield: 32.5% (acetate)
Molecular formula: $C_{10}H_{22}N_2O \cdot CH_3COOH$
Elementary analysis:

|  | C % | H % | N % |
|---|---|---|---|
| Calculated: | 58.5 | 10.6 | 11.4 |
| Found: | 58.4 | 10.58 | 11.4 |

Rf value: silica gel plate (n-butanol:acetic acid:-water=3:1:1), Rf=0.52
IR (Nujol): 1690, 1620 cm$^{-1}$ (—CO—NH—)

EXAMPLE 5

L-leucine-p-hydroxyphenylethylamide

Boc-Leu-OH.H$_2$O (49.9 g, 0.2 M) and HOSu (23.0 g, 0.2 M) were dissolved in THF (300 ml) in a 1 lit. round flask. DCC (41.3 g, 0.2 M) in THF (200 ml) solution was added dropwise at −10° C. for about 10 minutes and the mixture was stirred at room temperature overnight. Precipitated DCU was filtered off and the filtrate was concentrated. The residue was dissolved in ethyl acetate (300 ml), washed with 1 N-HCl, NaCl solution and a small amount of water and dried with anhydrous sodium sulfate. After removal of the drying agent, the solution was concentrated, and n-hexane was added thereto to obtain Boc-Leu-OSu as a colorless powder (m.p. 106°–110° C., 59.11 g, yield: 90%).

To tyramine (1.51 g, 11 mM) dissolved in DMF (15 ml) was added Boc-Leu-OSu (3.28 g, 10 mM) and DMF (5 ml), neutralized by adding NMM, and stirred overnight. DMF was distilled off in vacuo and ethyl acetate (100 ml) was added to the residue, which was then washed with 5% w/w sodium bicarbonate solution, NaCl solution, 1 N-HCl, NaCl solution and a small amount of water, and dried with anhydrous sodium sulfate. The drying agent was removed, and the solution was concentrated. Then n-hexane was added to the residue to obtain a precipitated powder (3.01 g). After drying, the powder was dissolved in dioxane (5 ml), and then 4.3 N-HCl/dioxane (dioxane absorbed with anhydrous hydrogen chloride) (5 ml) was added at 5° C. thereto, and the mixture was stirred for 2 hours at room temperature. Hydrogen chloride and dioxane were distilled off in vacuo. Then n-hexane was added to the oily residue at 0° C. to obtain the precipitate. The precipitate was dried in vacuo to yield L-leucine-p-hydroxyphenylethylamide.HCl powder (2.23 g).

Figure 8:
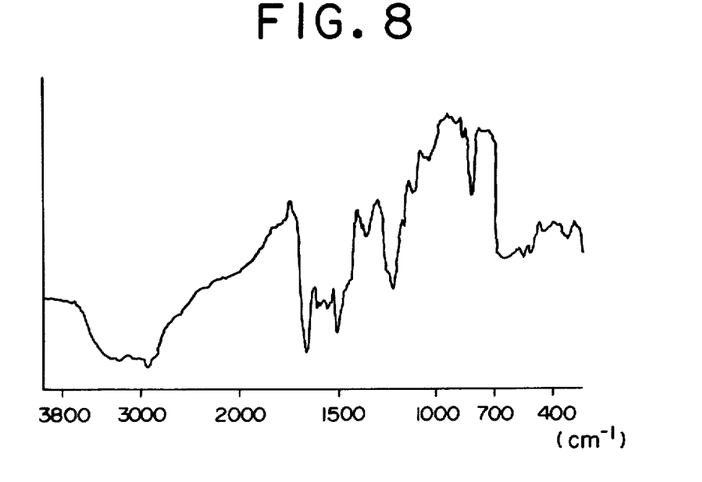
FIG. 8 is the IR spectrum of L-leucine-p-hydroxyphenylethylamide.

Yield: 78.0% (from Boc-Leu-OSu)
Molecular formula: $C_{14}H_{22}N_2O_2 \cdot HCl$
Elementary analysis:

|  | C % | H % | N % |
|---|---|---|---|
| Calculated: | 58.63 | 8.08 | 9.77 |
| Found: | 58.35 | 8.23 | 9.50 | m.p.: 125°–130° C.
IR spectrum: FIG. 8
TLC:
silica gel plate (merck, No. 5715)
developer: (n-butanol:pyridine:glacial acetic acid:-water=15:10:3:12)
Rf=0.70

EXAMPLE 6

L-leucine-p-hydroxyphenylethylamide

Ethyl chloroformate (0.94 ml, 10 mM) was added to Z-Leu-OH (2.7 g, 10 mM) and NMM (1.0 g, 10 mM) dissolved in THF (30 ml) at −20° C., and stirred at −15° C. for 2 minutes. Tyramine (1.4 g, 10 mM) in DMF (20 ml) was added thereto and the mixture was stirred at room temperature overnight. The solvent was removed in vacuo, ethyl acetate (100 ml) was added thereto, and the mixture was washed with 10% citrate solution, 5% w/w aqueous sodium bicarbonate and water, and dried with anhydrous sodium sulfate. After removal of the drying agent, n-hexane was added to the oily residue. The precipitate was recrystallized from ethyl acetate-n-hexane to yield a white powder (3.0 g, 78%). This powder was dissolved in 50% v/v aqueous ethanol (600 ml), 5% w/w palladium carbon (600 ml) and aqueous N-HCl (5 ml) were added, and hydrogen gas was introduced with stirring at room temperature. After the generation of carbon dioxide gas stopped, the catalyst was removed and the filtrate was concentrated. The colorless oily product was dried in vacuo to yield L-leucine-p-hydroxyphenylethylamide.HCl (1.8 g, 62.7%).

EXAMPLE 7

L-leucine-p-hydroxyphenylethylamide

Boc-Leu-OSu (3.28 g, 10 mM) and tyramine (1.37 g, 10 mM) were dissolved in DMF (30 ml), adjusted to pH 7 by adding NMM and the mixture was stirred at room temperature overnight. After DMF was removed, the residue was dissolved in ethyl acetate (50 ml) and washed three times with aqueous 5% w/w sodium bicarbonate, twice with 1 N-HCl, twice with water and sodium sulfate. Ethyl acetate was removed and the residue was charged on a column of silica gel (100 g), then eluted with benzene-ethyl acetate (1:1) to obtain Boc-leu-NHCH$_2$-CH$_2$-C$_6$H$_4$-OH (1.58 g). This compound (1.4 g) was dissolved in trifluoroacetic acid (5 ml), stirred for 30 minutes at room temperature and the trifluoroacetic acid was removed. The residue was dissolved in 0.1 N acetic acid and charged on a column of Sephadex LH-20 (97.0×3.0 cm), then fractionated to fractions of 6.3 ml each. Fractions Nos. 30-38 were collected and lyophilized to yield L-leucine-p-hydroxyphenylethylamide acetate [1.25 g, yield: 40.3%, molecular formula: C$_{14}$H$_{22}$N$_2$O$_2$.CH$_3$COOH, TLC: (silica gel plate, n-butanol:acetic acid:water=3:1:1), Rf=0.75].

EXAMPLE 8

L-alanine-p-hydroxyphenylethylamide

Boc-Ala-OH (37.8 g, 0.2 M) and HOSu (23.0 g, 0.2 M) were dissolved in THF (300 ml) in a 1 lit. round flask. DCC (41.3 g, 0.2 M) in THF (200 ml) solution was added dropwise at −10° C. for about 10 minutes and the mixture was stirred at room temperature overnight. Precipitated DCU was filtered off and the filtrate was concentrated. The residue was dissolved in ethyl acetate (300 ml), washed with 1 N-HCl, NaCl solution and a small amount of water and dried with anhydrous sodium sulfate. After removal of the drying agent, the solution was concentrated, and n-hexane was added thereto to obtain a colorless powder (52.7 gm, m.p. 140°-143° C., yield: 91%).

Boc-Ala-OSu (2.86 g, 10 mM) and DMF (5 ml) were added to tyramine (1.51 g, 11 mM) dissolved in DMF (20 ml); and after neutralizing by adding NMM, the mixture was stirred overnight. DMF was distilled off in vacuo and ethyl acetate (100 ml) was added to the residue, which was then washed with 5% w/w sodium bicarbonate solution, NaCl solution, 1 N-HCl, NaCl solution and a small amount of water, and dried with anhydrous sodium sulfate. The drying agent was removed, and the solution was concentrated. n-Hexane was added to the oily residue to obtain a powder (2.55 g).

This latter powder was dissolved in dioxane (5 ml), and 4.3 N-HCl/dioxane solution (5 ml) was added thereto at 5° C., and then the mixture was stirred at room temperature for 2 hours. Hydrogen chloride and dioxane were distilled off in vacuo. n-Hexane was added to the oily residue at 0° C. to obtain a precipitate. The precipitate was dried in vacuo to yield a powder of L-alanine-p-hydroxyphenylethylamide.HCl (1.81 g).

Figure 9:
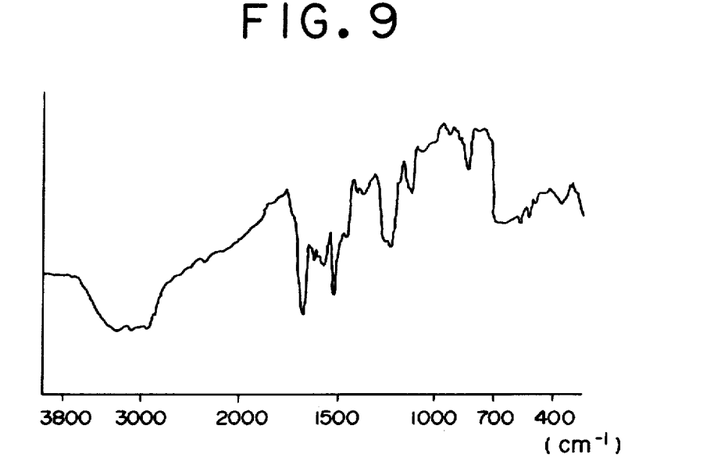
FIG. 9 is the IR spectrum of L-alanine-p-hydroxyphenylethylamide.

Yield: 74.0% (from Boc-Ala-OSu)
Molecular formula: C$_{11}$H$_{16}$N$_2$O$_2$.HCl
Elementary analysis:

|  | C % | H % | N % |
|---|---|---|---|
| Calculated: | 53.99 | 6.95 | 11.45 |
| Found: | 53.78 | 7.11 | 11.23 | m.p.: 105°-110° C.
IR spectrum: FIG. 9
TLC:
  silica gel plate (Merck, No. 5715)
  developer (n-butanol:pyridine:glacial acetic acid:water=15:10:3:12)
Rf=0.64

EXAMPLE 9

L-alanine-p-hydroxyphenylethylamide

Ethyl chloroformate (0.94 ml) was added to Z-Ala-OH (2.2 g, 10 mM) and NMM (1.0 g, 10 mM) in THF at −20° C. and the mixture was stirred at −15° C. for 2 minutes. Tyramine (1.4 g, 10 mM) in DMF (20 ml) was added thereto and the mixture was stirred at room temperature overnight. THF was distilled off and ethyl acetate (100 ml) was added. The solution was washed with 10% w/w aqueous citrate, 5% w/w aqueous sodium bicarbonate and a small amount of water and dried with anhydrous sodium sulfate. After the drying agent was removed, n-hexane was added to the oily residue obtained from the concentrated solution. The precipitate was recrystallized from ethyl acetate-n-hexane to obtain a white powder. This powder was dissolved in 50% aqueous ethanol (600 ml), 5% palladium carbon (600 mg) and N-HCl (5 ml) were added, and hydrogen gas was introduced with stirring at room temperature. After the generation of carbon dioxide has terminated, the catalyst was removed and the filtrate was concentrated and dried in vacuo to yield L-alanine-p-hydroxyphenylethylamide.HCl (1.1 g, 46.1%).

EXAMPLE 10

LAP activity assay using L-leucine-benzylamide and amine oxidase

A phosphate buffer solution (pH 7.0, 1 ml) of L-leucine-benzylamide (50 mM) was introduced into a reaction vessel provided with an oxygen electrode. LAP sample (50 μl, 50 U/ml, 100 U/ml, 150 U/ml, 200 U/ml and 250 U/ml) (Boehringer G.m.b.H.) was added thereto, and the mixture was incubated at 37° C. for 15 minutes with stirring. Amine oxidase (2 U/ml, Miles Lab., 50 μl) was added and the mixture was incubated for one minute at 37° C. The benzylamine formed by the LAP was oxidized and the amount of consumed oxygen gas measured with an oxygen electrode as an electric current variation.

Figure 1:
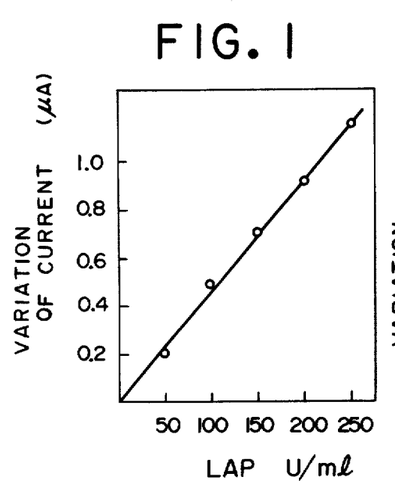
FIG. 1 is a LAP assay curve by oxygen electrode using L-leucine-benzylamide and amine oxidase.

The result is shown in FIG. 1 in which the variation of electric current is in proportion to LAP activity. LAP activity can thus be determined by measuring electric current variation.

EXAMPLE 11

Figure 2:
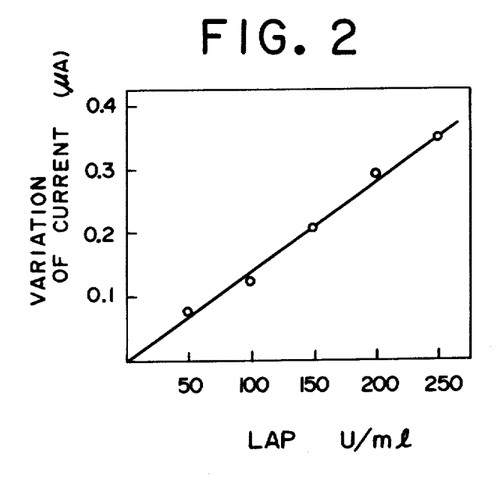
FIG. 2 is a LAP assay curve by oxygen electrode using L-leucine-p-hydroxyphenylethylamide and tyramine oxidase.

LAP activity assay using L-leucine-p-hydroxyphenylethylamide and tyramine oxidase The substrate solution and enzyme in Example 10 were replaced by a 0.1 M phosphate buffer solution (pH 7.0, 1 ml) of L-leucine-p-hydroxyphenylethylamide (50 mM) and tyramine oxidase (3 U/ml, produced by *Sarcina lutea* IAM 1099, 50 μl), and the process was carried out the same as in Example 10 for LAP activity assay. The result is shown in FIG. 2, which shows good results.

EXAMPLE 12

LAP activity assay using L-leucyl-D-methionine and D-amino acid oxidase

Figure 3:
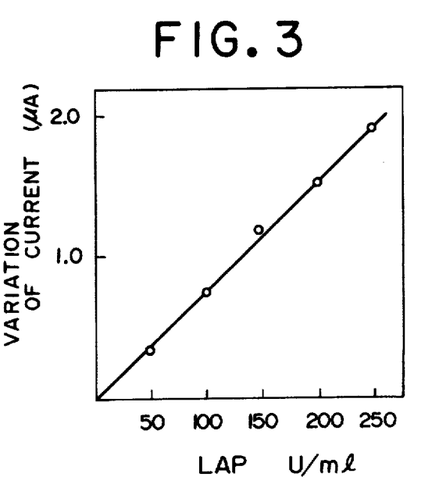
FIG. 3 is a LAP assay curve by oxygen electrode using L-leucyl-D-methionine and D-amino acid oxidase.

The substrate solution and enzyme of Example 10 were replaced by a 0.1 M phosphate buffer solution (pH 7.0, 1 ml) of L-leucyl-D-methionine (50 mM) and D-amino acid oxidase (11.5 U/ml, Boehinger G.m.b.H., 10 μl), and the process was carried out the same as in Example 10 for LAP activity assay. The result is shown in FIG. 3.

EXAMPLE 13

LAP activity assay using L-leucine-n-butylamide and amine oxidase

Figure 4:
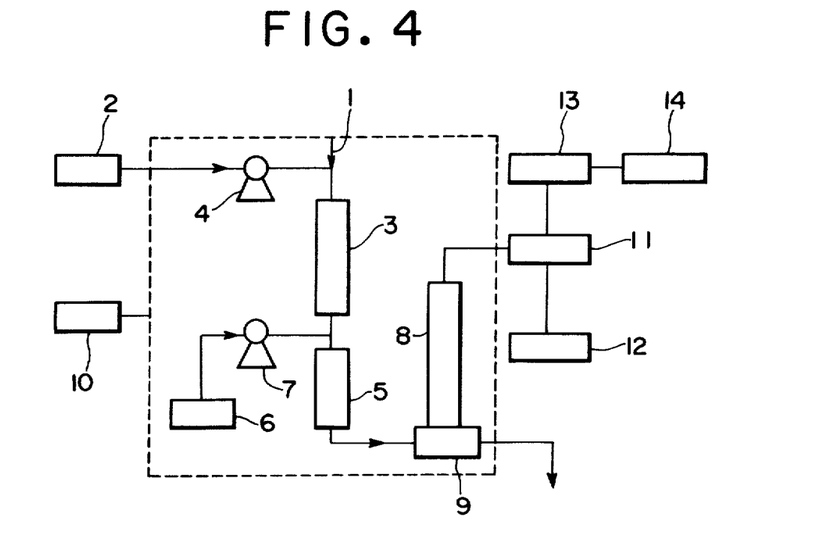
FIG. 4 is a flow diagram for a LAP activity assay system.

FIG. 4 illustrates the flow diagram for a LAP activity assay system.

The LAP activity assay sample added through sample injector 1 and substrate solution 2 are introduced into LAP reactor vessel 3. The sample is introduced by using a micropipette or an autosampler and the substrate solution is added by constant volume pump 4. After incubation, the reaction mixture is transferred to immobilized enzyme column 5 wherein simultaneously the buffer solution in buffer vessel 6 is supplied through constant volume pump 7.

The solution passed through the immobilized enzyme column is transferred into flow cell 9 wherein an electrode 8 such as an oxygen electrode or a hydrogen peroxide electrode for measuring consumed oxygen or liberated hydrogen peroxide by enzymatic action is provided. These are kept at constant temperature in constant temperature vessel 10. The electric variation detected by electrode 8 is recorded in recorder 12, digital meter 13 or digital recorder 14 through amplifier 11.

In the above flow diagram, the following were used:
Substrate solution: 0.1 M phosphate buffer (pH 7.0) of L-leucine-n-butylamide (50 mM); LAP activity assay sample: LAP solutions of various concentrations (50 U/ml, 100 U/ml, 150 U/ml, 200 U/ml and 250 U/ml); immobilized enzyme column: 2.8×30 mm containing 100 mg of immobilized amine oxidase (15 U/g carrier), covalently bonded with amine oxidase and porous polymer (carrier: polyacrylnitrile, cross-linking reagent: glutaraldehyde, British Patent No. 2,015,001); and flow-cell: 0.1 ml inner volume, provided with an oxygen electrode.

A LAP sample (10 μl) was added to the substrate solution (50 μl) and incubated at 37° C. for 15 minutes. 0.1 M phosphate buffer (pH 7.0) flowed at a rate of 1 ml/min. into immobilized enzyme column 5 from buffer vessel 6. After the amount of dissolved oxygen detected by oxygen electrode 8 became constant in flow cell 9, the incubation mixture (10 μl) was transferred into the immobilized enzyme column 5. The n-butylamine formed by the LAP was oxidized by the immobilized enzyme and the amount of dissolved oxygen consumed in the enzymatic reaction was measured by oxygen electrode 8 in flow cell 9 as an electric current variation which was recorded through amplifier 11.

Figure 5:
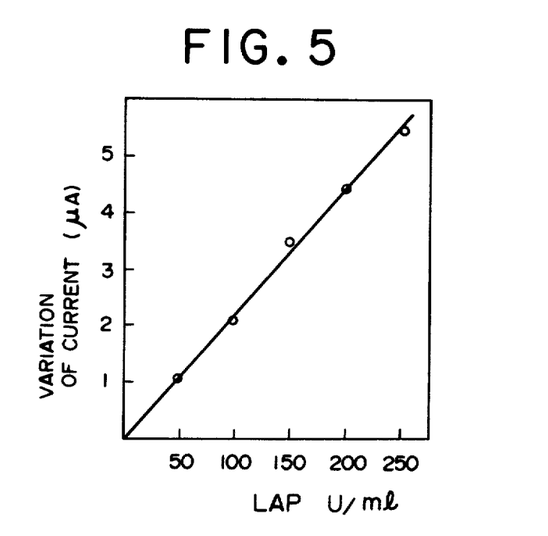
FIG. 5 is a LAP assay curve by oxygen electrode of the flow diagram of FIG. 4 using L-leucine-n-butylamide and amine oxidase.

The result is shown in FIG. 5 wherein good results were obtained which are advantageous for automatic analysis.

EXAMPLE 14

LAP activity assay using L-leucyl-D-methionine and D-amino acide oxidase

Figure 6:
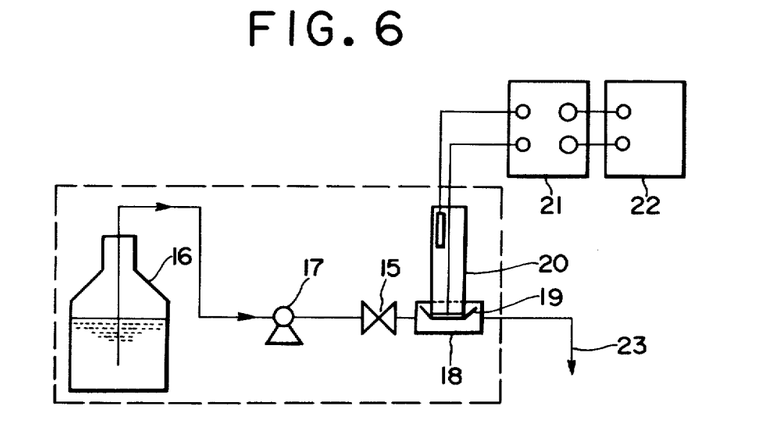
FIG. 6 is a diagrammatic showing of LAP assay equipment.

LAP samples (50 U/ml, 100 U/ml, 150 U/ml, 200 U/ml and 250 U/ml) (10 μl) were added to 0.1 M phosphate buffer solutions (pH 7.0, 50 μl) of L-leucyl-D-methionine (50 mM), and incubated at 37° C. for 15 minutes. The LAP activity was measured by the system shown in FIG. 6. In FIG. 6, 15 indicates an injector for the LAP incubation mixture, 16 indicates a 0.1 M phosphate buffer vessel, 17 indicates a constant volume pump which transfers the buffer at a flow rate 1 ml/min., and 18 indicates the flow cell. The flow cell consists of a reactor-detector provided with oxygen electrode 20 having an immobilized enzyme membrane 19 of D-amino acid oxidase (carrier: polyacrylnitrile membrane containing an amino group; cross-linking reagent: glutaraldehyde, British Patent No. 2,015,001) (30 U/g carrier, diameter 5 mm, 0.8 mg, D-amino acid oxidase activity 2.4 mU). Electric current variation detected by the oxygen electrode was recorded in recorder 22 through amplifier 21. Numeral 23 indicates the exhaust outlet.

In the above apparatus, 0.1 M phosphate buffer (pH 7.0) flowed at 1 ml/min., and after dissolved oxygen has stabilized, the above LAP incubation mixture (10 μl) was injected through injector 15. D-methionine liberated by LAP action was oxidized by the enzymatic action of immobilized enzyme membrane 19 to consume dissolved oxygen which was detected by oxygen electrode 20 and the electric current variation was recorded.

Figure 7:
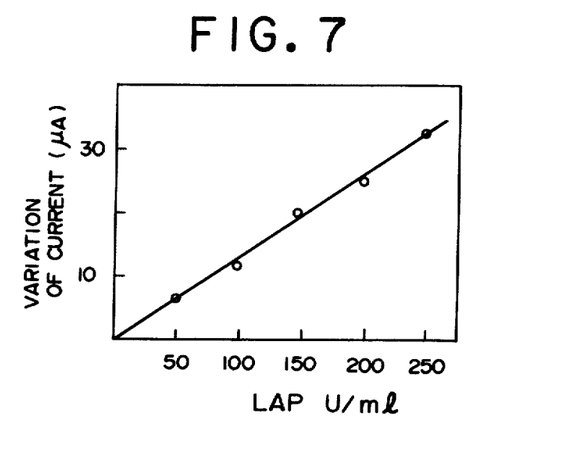
FIG. 7 is a LAP assay curve by enzyme electrode provided with immobilized enzyme and oxygen electrode, and using L-leucyl-D-methionine and D-amino acid.

The result is shown in FIG. 7, wherein good results were obtained for the automatic assay system.

Furthermore, LAP activity was continuously assayed 100 times using LAP activity assay samples (100 U/ml and 200 U/ml). After each respective assay, the amount of dissolved oxygen had immediately (one minute after finishing the detection) shown the original stable value and each of the 100 assays revealed the same good results and reproducibility.

EXAMPLE 15

Substrate specificity on various synthetic substrates by LAP and aminopeptidase

Synthetic substrate of the following were used: L-leucinamide (50 mM), L-leucine-p-nitroanilide (50 mM), L-leucine-β-naphthylamide (saturated solution), L-leucine-n-butylamide (50 mM) and L-leucine-p-hydroxyphenylethylamide (50 mM).

A 0.1 M phosphate buffer solution (pH 7.0, 10 μl) containing LAP (300 U/ml) was added to a 0.1 M phosphate buffer solution (pH 7.0, 50 μl) of the above substrate, and the mixture was incubated at 37° C. for 15 minutes.

Also aminopeptidase (20 U/ml, 10 μl, Boehringer G.m.b.H.) was used under the same conditions.

The L-leucine liberated by the LAP and aminopeptidase was measured by the system shown in FIG. 4 as specified in Example 13, except that L-amino acid oxidase was used in place of amine oxidase. A 0.1 M phosphate buffer (pH 7.0) was fed at 1 ml/min. by the constant volume pump; and after dissolved oxygen in the flow cell reached the stable state, the above incubation mixture (10 μl) was injected. A column of immobilized L-amino acid oxidase fibers (28 U/g-carrier, 100 mg, 2.8×30 mm) was used. Consumed oxygen corresponding to the formation of L-leucine by L-amino acid oxidase was detected by the oxygen electrode in the flow cell, which was amplified to change the electric current variation; and the action of LAP and aminopeptidase on various substrates was thus assayed. The results are shown in Table 1.

TABLE 1

|  | LAP | Aminopeptidase |
|---|---|---|
| L-leucinamide | +++ | +++ |
| L-leucine-p-nitroanilide | + | +++ |
| L-leucine-β-naphthylamide | + | +++ |
| L-leucine-n-butylamide | +++ | + |
| L-leucine-p-hydroxy-phenylethylamide | +++ | +± |

As shown in Table 1, previously known L-leucinamide, N-L-leucyl-p-nitroanilide and L-leucine-β-naphthylamide were hydrolyzed not only by LAP but also by aminopeptidase, and hence these substrates are less preferable for LAP-activity assay in serum because of containing LAP and aminopeptidase. On the contrary, since L-leucine-n-butylamide and L-leucine-p-hydroxyphenylethylamide of the present invention were hydrolyzed by LAP and almost not hydrolyzed by aminopeptidase, these substrates are preferable for serum LAP assay.

EXAMPLE 16

LAP activity assay using L-leucine-p-hydroxyphenylethylamide and amine oxidase

A substrate solution (50 mM) was prepared by dissolving L-leucine-p-hydroxyphenylethylamide hydrochloride obtained as in Example 5 in 0.1 M phosphate buffer (pH 7.0). The following solution [I] was prepared.

| | |
|---|---|
| 0.2 M Tris-HCl buffer (pH 8.0) | 0.1 ml |
| 0.3% 4-aminoantipyrine | 0.05 ml |
| 0.2% phenol | 0.05 ml |
| 0.5 mg/ml peroxidase (Sigma Chem. Co. Type-I) | 0.05 ml |
| 0.1 M magnesium chloride | 0.025 ml |
| 50 mM substrate solution (L-leucine-p-hydroxyphenylethylamide) | 0.025 ml |
| distilled water | 0.1 ml |
| Solution [I]  Total | 0.4 ml |

A reaction composition solution [II] (0.45 ml) was prepared by adding amine oxidase (5 U/ml, Miles Lab., 50 μl) in the above solution [I] (0.4 ml).

Normal rat serum*, parenchymal liver disease model rat serum and extrahepatic cholestasis liver model rat serum*, each respectively 50 μl, were added to the reaction composition solution [II] (0.45 ml), and the mixture was incubated at 37° C. for 30 minutes and spectrophotometrically measured at 480 nm.

*serum of Wister rat, male, weight about 250 g.
**50% carbon tetrachloride-olive oil (V/V) (1 ml/kg/day) was subcutaneously injected twice in a week for 4 weeks into backside of Wister rat, male, weight about 250 g. Serum was collected after 48 hours from the final administration.
***Wister rat, male, weight about 250 g was etherized, and the common bile duct was ligated. Serum was collected after 48 hours from ligation.

Serum of known LAP activity (Seraclea N, 122 G-R units, Nihon Shoji Co.) was treated as the same way hereinabove and the LAP activity calculated. The result is shown in Table 2.

In comparison with the above assay method, a known LAP activity assay method (Wako Pure Chem. Co., Code 274-41901, substrate: L-leucine-p-diethylaminoanilide) was applied to the same serum sample. The result is shown in Table 2.

TABLE 2

| | Substrate | |
|---|---|---|
| Serum sample | L-leucine-p-hydroxy-phenylethylamide (G-R unit) | L-leucine-p-diethylaminoanilide (G-R unit) |
| normal rat | 331 | 148 |
| parenchymal liver disease model rat | 2486 | 237 |
| extrahepatic cholestasis liver model rat | 379 | 241 |

As shown in the table, L-leucine-p-hydroxyphenylethylamide of the present invention can be used as an advantageous substrate for the diagnosis of parenchymal liver disease.

EXAMPLE 17

LAP assay using L-alanine-p-hydroxyphenylethylamide and amine oxidase

L-alanine-p-hydroxyphenylethylamide hydrochloride obtained as in Example 8 was dissolved in 0.1 M phosphate buffer (pH 7.0) to prepare a substrate solution (50 mM). The substrate solution (0.025 ml) was used in place of the substrate solution of Example 16 and solution [I] and reaction composition solution [II] were prepared in the same way as in Example 16. LAP activity was assayed the same as in Example 16. The result is shown in Table 3.

TABLE 3

| Serum | Substrate L-alanine-p-hydroxyphenylethylamide (G-R unit) |
|---|---|
| normal rat | 117 |
| parenchymal liver disease model rat | 165 |
| extrahepatic cholestasis liver model rat | 219 |

As shown in the table, L-alanine-p-hydroxyphenylethylamide of the present invention is a preferable synthetic substrate for diagnosis of extrahepatic cholestasis of the liver.

EXAMPLE 18

| | |
|---|---|
| 0.2 M Tris-HCl buffer (pH 8.0) | 0.1 ml |
| 0.3% 4-aminoantipyridine | 0.05 ml |
| 0.2% phenol | 0.05 ml |
| 0.05% peroxidase (Sigma Chem. Co. Type II) | 0.05 ml |
| 0.1 M magnesium chloride | 0.025 ml |
| 50 mM L-leucine-p-hydroxy-phenylethylamide | 0.025 ml |
| amine oxidase (7.6 U/ml) | 0.01 ml |
| distilled water | 0.14 ml |
| Total | 0.45 ml |

Figure 10:
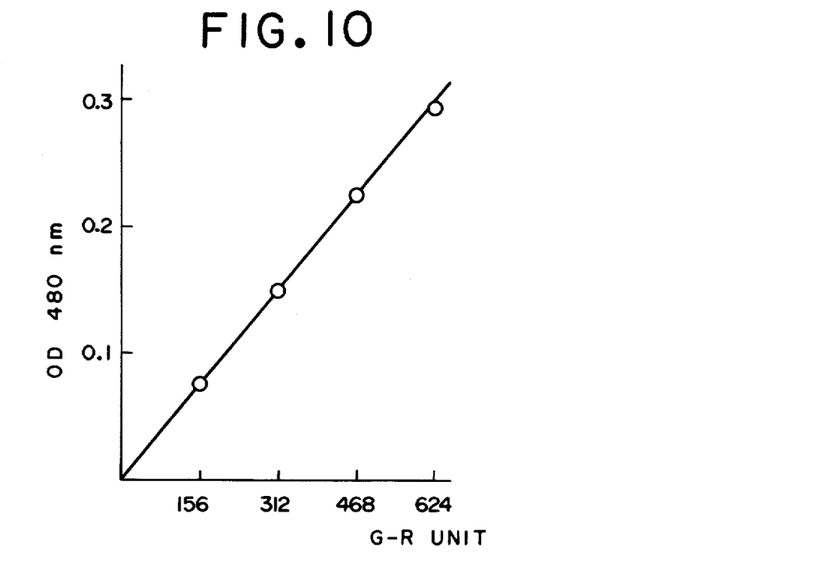
FIG. 10 is a standard curve using L-leucine-p-hydroxyphenylethylamide.

A standard serum [Wako Pure Chem. Co., Standard LAP assay serum, LAPC-Test Wako (L-leucine-p-diethylaminoanilide substrate method), 50 μl] was added to the above reaction composition solution and the mixture was incubated at 37° C. for 30 minutes. Ethanol (2.5 ml) was added to stop the reaction. A sedimented substance was separated and the supernatant solution was colorimetrically measured at 480 nm. The standard curve is shown in FIG. 10. A linear relation between LAP activity and absorption at 480 nm was observed.

The method can be used as a quantitative assay method of serum LAP activity using an assay kit.

Figure 11:
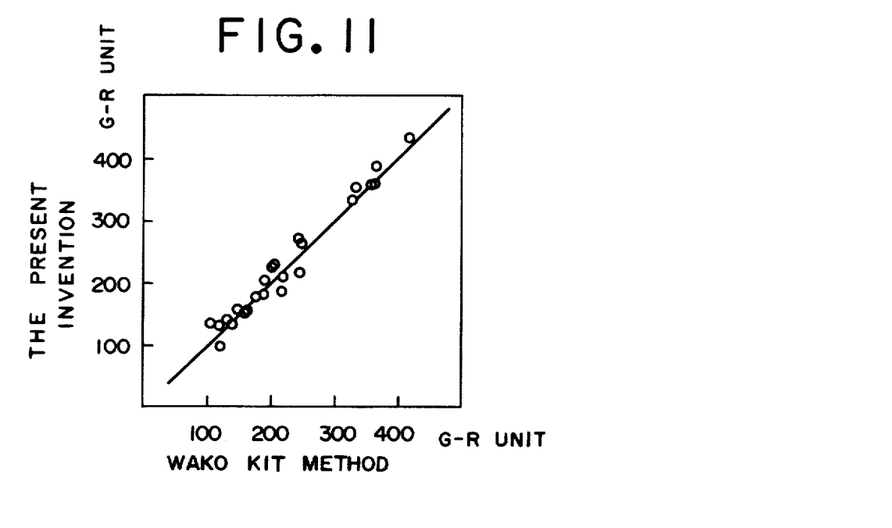
FIG. 11 is a correlation curve using L-leucine-p-hydroxyphenylethylamide and a commercial sample.

Serum LAP activity of human patients was assayed by the above standard curve. A correlation coefficient $\gamma=0.984$ [sample n=24] and a regression equation $Y=1.024X-2.898$, which are good results, were observed. The correlation curve is shown in FIG. 11.

What is claimed is:

1. Assay method for leucine aminopeptidase which comprises reacting a substrate amide compound or salt thereof of the formula $$R_1-\underset{\underset{NH_2}{|}}{CH}-CO-R_2$$

wherein $R_1$ is lower alkyl and $R_2$ is substituted methylamino or D-amino acid residue, with a sample for leucine aminopeptidase assay, oxidizing the thus-liberated, substituted methylamine or D-amino acid by the corresponding oxidase, and measuring the thus-consumed oxygen or liberated hydrogen peroxide.

2. An assay method as claimed in claim 1, wherein $R_1$ is isobutyl.

3. An assay method as claimed in claim 1, wherein $R_1$ is methyl.

4. An assay method as claimed in claim 1, wherein $R_2$ is substituted methylamino of the formula $$-NH-CH_2-R_3$$

in which $R_3$ is organic.

5. An assay method as claimed in claim 4, wherein $R_3$ is selected from the group consisting of methyl, ethyl, n-propyl, isopropyl, n-butyl, amyl, p-hydroxybenzyl, 3,4-dihydroxybenzyl, 5-imidazolemethyl, 3-indolemethyl and phenyl.

6. An assay method as claimed in claim 1, wherein $R_2$ is a D-amino acid residue of the formula $$-NH-C^*H\begin{smallmatrix}\diagup R_4 \\ \diagdown R_5\end{smallmatrix}$$

in which one of $R_4$ or $R_5$ is carboxyl, the other is an organic residual group, and C* is a D-asymmetric carbon atom.

7. An assay method as claimed in claim 6, wherein one of $R_4$ and $R_5$ in D-amino acid residue is carboxyl, the other is selected from the group consisting of methylthioethyl, isobutyl, methyl or phenyl, and C* is a D-asymmetric carbon atom.

8. An assay method as claimed in claim 1, wherein the said oxidase is immobilized enzyme.

9. An assay method as claimed in claim 1, wherein the said assay is carried out by oxygen electrode or hydrogen-peroxide electrode, or enzyme electrode thereof.

10. An assay method as claimed in claim 1, wherein the said method comprises measuring hydrogen peroxide by coloration reagent or luminescent reagent.

* * * * *